US012746195B2

(12) United States Patent
Frechet et al.

(10) Patent No.: US 12,746,195 B2
(45) Date of Patent: Sep. 29, 2026

(54) ***BERTHOLLETIA EXCELSA* EXTRACT AND USE THEREOF**

(71) Applicants: CLARIANT INTERNATIONAL LTD, Muttenz (CH); Clariant Brasil LTDA., São Paulo (BR)

(72) Inventors: Mathilde Frechet, Toulouse (FR); Hanane Chajra, Tournefeuille (FR); Sandrine Delaunois, Toulouse (FR); Benoit Mignard, Toulouse (FR); Daniel Nosé Sabará, São Paulo (BR); Maria Célia Hibari Reimberg, São Paulo (BR); Stephanie Ferreira Sanches Lopes, São Paulo (BR); Bruna Aline Da Silva Merigiolli, São Paulo (BR); Robson José Da Silva Cruz, São Paulo (BR)

(73) Assignees: CLARIANT INTERNATIONAL LTD, Muttenz (CH); Clariant Brasil LTDA., Sao Paulo (BR)

( * ) Notice: Subject to any disclaimer, the term of this patent is extended or adjusted under 35 U.S.C. 154(b) by 423 days.

(21) Appl. No.: 18/275,798

(22) PCT Filed: Jan. 17, 2022

(86) PCT No.: PCT/EP2022/050828

§ 371 (c)(1),
(2) Date: Aug. 3, 2023

(87) PCT Pub. No.: WO2022/167202

PCT Pub. Date: Aug. 11, 2022

(65) Prior Publication Data

US 2024/0091132 A1 Mar. 21, 2024

(30) Foreign Application Priority Data

Feb. 4, 2021 (EP) .................................... 21305152

(51) Int. Cl.

| | |
|---|---|
| ***A61K 36/00*** | (2006.01) |
| ***A61K 8/34*** | (2006.01) |
| ***A61K 8/9789*** | (2017.01) |
| ***A61K 31/05*** | (2006.01) |
| ***A61K 36/185*** | (2006.01) |
| ***A61P 17/04*** | (2006.01) |
| ***A61P 17/06*** | (2006.01) |
| ***A61Q 19/10*** | (2006.01) |

(52) U.S. Cl.

CPC ............ *A61K 8/9789* (2017.08); *A61K 8/347* (2013.01); *A61K 31/05* (2013.01); *A61K 36/185* (2013.01); *A61P 17/04* (2018.01); *A61P 17/06* (2018.01); *A61Q 19/10* (2013.01); *A61K 2236/15* (2013.01); *A61K 2236/333* (2013.01)

(58) Field of Classification Search

CPC ........................................................ A61K 31/05
See application file for complete search history.

(56) References Cited

U.S. PATENT DOCUMENTS

| | | | |
|---|---|---|---|
| 6,471,972 | B1 | 10/2002 | Bonte et al. |
| 7,887,858 | B2 | 2/2011 | Cauchard et al. |
| 2014/0090660 | A1 | 4/2014 | Xavier et al. |

FOREIGN PATENT DOCUMENTS

| | | | |
|---|---|---|---|
| CN | 111973496 | A | 11/2020 |
| DE | 69611082 | T2 | 5/2001 |
| DE | 102016009036 | A1 | 1/2018 |
| EP | 0809484 | A2 | 12/1997 |
| FR | 2752527 | A1 | 2/1998 |
| KR | 10-1987421 | B1 | 6/2019 |
| WO | 1996/25143 | A1 | 8/1996 |
| WO | 2009082796 | A1 | 7/2009 |

OTHER PUBLICATIONS

Behrens, Clariant's Ethience Boosts Skin Barrier Function. Cosmetics & Toiletries. Retrieved online at: https://www.cosmeticsandtoiletries.com/cosmetic-ingredients/actives/news/21844214/clariant-international-ltd-clariants-ethience-boosts-skin-barrier-function. 3 pages, Apr. 16, 2021.
Davies et al., Development of an in vitro model for studying the penetration of chemicals through compromised skin. Toxicol In Vitro. Feb. 2015;29(1):176-81.
Gomes et al., Optimized extraction of polyphenolic antioxidant compounds from Brazil nut (*Bertholletia excelsa*) cake and evaluation of the polyphenol profile by HPLC. J Sci Food Agric. Jun. 2016;96(8):2805-14.
Kezic et al., Absorption of chemicals through compromised skin. Int Arch Occup Environ Health. May 2009;82(6):677-88.
Liu et al., The IL-23/IL-17 Pathway in Inflammatory Skin Diseases: From Bench to Bedside. Front Immunol. Nov. 17, 2020;11:594735, 13 pages.
Martinez et al., Role of proteoglycans on skin ageing: a review. Int J Cosmet Sci. Dec. 2020;42(6):529-535.
International Search Report and Written Opinion for Application No. PCT/EP2022/050828, dated Jul. 11, 2022, 11 pages.

*Primary Examiner* — Qiuwen Mi
(74) *Attorney, Agent, or Firm* — McCarter & English, LLP; Wei Song

(57) ABSTRACT

The present invention relates to an extract of *Bertholletia excelsa* seeds obtained from extracting an at least partly deoiled press residue of *Bertholletia excelsa* seeds and to a method for preparing such extract. Furthermore, the present invention refers to a cosmetic or pharmaceutic composition comprising such extract as active ingredient and to the use of the extract or the composition for skin care.

12 Claims, 4 Drawing Sheets

*BERTHOLLETIA EXCELSA* EXTRACT AND USE THEREOF

CROSS-REFERENCE TO RELATED APPLICATIONS

This application is a U.S. national stage application, filed under 35 U.S.C. § 371(c), of International Application No. PCT/EP2022/050828, filed on Jan. 17, 2022, which claims priority to European Patent Application No. 21305152.7, filed on Feb. 4, 2021.

The present invention relates to an extract of *Bertholletia excelsa* seeds obtained from extracting an at least partly deoiled press residue of *Bertholletia excelsa* seeds and to a method for preparing such extract. Furthermore, the present invention refers to a cosmetic or pharmaceutic composition comprising such extract as active ingredient and to the use of the extract or the composition for skin care and hair care.

At the interface between the organism and the environment, the skin—composed of three distinct layers: the stratum corneum (hereinafter called "SC"), the epidermis and the dermis—provides a mechanical protection and represents the first barrier against aggressions from the outside and against uncontrolled loss of body fluids. External aggressions are, for example, ultra-violet and infra-red exposure, particles matters' pollution, pathogens, allergens, fluctuation of temperature and humidity, chemicals products, mechanical constraints due to daily habits such as shaving, gloves, and mask wearing due to sanitary decline of our environment by the prevalence of harmful viruses. Additionally, the skin protects also the organism against internal aggressions such as chronological aging, genetic factors, hormonal fluctuation and immune deregulation. However, and because the skin is also continuously exposed to the environment when those aggressions become too excessive, they may deteriorate the skin and actively contribute to the development of a compromised skin (Kezic and Nielsen, Int. Arch. Occup. Environ. Health, 2009, 82:677-688). Moreover, many dermatological pathologies may be classified as compromised skin conditions such as eczema, contact dermatitis, atopic dermatitis, psoriasis and ichthyosis (Kezic and Nielsen, Int. Arch. Occup. Environ. Health, 2009, 82:677-688). In such situations, the skin protective function also known as skin barrier function is impaired. Thus, as previously exposed, compromised skins, a common affliction, may occur through a multi-factorial process driven by the aforementioned external and internal aggressions. Beside the typical poor barrier function, characterized in the increase of trans-epidermal water loss (TEWL), it has been demonstrated that the characteristics of compromised skins may be visible signs such as dryness, redness, aberrant pigmentation and sebum-deregulation, itching and inflammation. Moreover, these compromised skins may be exposed to an enhanced penetration of harmful components coming from the environment as well as an increase of the water loss, leading to the maintenance of a deleterious and vicious circle (Davies et al, Toxicology in Vitro, 2015, 29:176-18199.

The SC made up of dead keratinized cells, surrounded by intercellular space filled with lipids plays a crucial role in the skin barrier function. Indeed, the SC acts as a shield and prevents the penetration of most substances into the deeper viable layers of the skin, and it prevents the water loss from the skin as well. It is agreed that SC's lipids may be responsible of these skin barrier functions and skin hydration properties. It is known that the skin surface lipids encompass glycerides, free fatty acids, wax esters, ceramides, cholesterol, squalene and phospholipids. The major lipids responsible for skin barrier function may be cholesterol, fatty acids, sphingolipids and ceramides. This lipidic barrier is known to be altered with aging and in some skin pathologies such as xerosis or atopic dermatitis. Poor skin barrier function is generally associated to these skin pathological conditions and in aging. Unfortunately, this skin lipidic barrier may also be altered by the aforementioned aggressions. Thus, it may not be able to perform its protective function optimally and may lead eventually to compromised skins. However, in non-compromised dry skin or normal skin, or non-pathological skin, the skin lipids could be altered mainly by external aggressions.

Besides the SC, the skin barrier function is also attributed to the whole epidermis, a stratified epithelium with a basal layer of proliferative cells and multiple suprabasal layers of differentiated keratinocytes. In the epidermis, two major constituents found also in any epithelial tissue layer may be dedicated to the prevention of entering and leaving of substances: the epithelial cells themselves and the tight junctions (hereinafter called "TJs").

It is known that TJs, found in all epithelial tissues, form a belt-like adhesion between cells, allowing the passage of only small molecules and ions. In human body, TJs may be composed of transmembrane proteins, namely the claudins, the occludin, the tricellulin, the Junction Adhesion Molecule (JAM) and the cytoplasmic plaque (ZO proteins). As mentioned above, epithelial cells themselves may be player for tissue barrier function. In the case of skin, the epithelial cells called keratinocytes, thanks to their cytoskeleton, ensure the maintenance of an adapted skin barrier function. Keratinocytes assemble massive amounts of cytoskeletal filaments that may be in part anchored to intercellular junctions, such as desmosomes, TJs and adherent junctions. These elements have been described to contribute to the mechanical stability and optimal elasticity of the epithelium. Moreover, as the epidermis is constantly in renewal, keratinocytes may be submitted to a complete process of differentiation as they may be progressing towards the surface. In the course of this differentiation process, keratinocytes undergo profound changes in cell shape, in height and packing geometry that affect their mechanic-physical properties, solidity and resistance. The differentiation process has been demonstrated to be entirely supported by the cytoskeleton. Furthermore, differentiated keratinocytes obtained thanks to differentiation process secrete the content of lamellar bodies with a unique lipid and protein composition. The differentiation process may, thus, be responsible for the maintenance of skin barrier protection, by providing continuously the SC in lipidic and proteic components. In addition to its structural function, cytoskeleton also has been demonstrated to support proliferation and migration of cells as well as their adhesion, and thus it regulates epidermal cohesion and its permeability.

As described above, a compromised barrier may allow the entry of substances into the skin. This may contribute and promote inflammatory processes in the skin. Indeed, these inflammatory processes may be the consequence of resident skin cells response and immune cells recruitment that produce proinflammatory molecules such as interleukins, tumor necrosis factor-α, granulocyte-macrophage colony-stimulating factor (CSF-1). Moreover, deregulated expression of the cytokines and chemokines in skin may contribute to dysfunctions of the epidermal barrier function as it is observed in aged skins and in many skin diseases, including atopic dermatitis and psoriasis associated with a strong water loss and dryness (Liu et al., Frontiers in Immunology, 2020, 11:

Article No. 594735). Additionally, inflammation process may occur also through inflammasome activation that cleaves the proinflammatory cytokines pro-IL-1β and pro-IL-18 into their active forms, which may be upregulated in these inflammatory skin diseases harboring poor barrier function, including psoriasis, vitiligo, systemic lupus erythematosus (SLE), and atopic dermatitis (AD). The same proinflammatory cytokines are described to be upregulated in aged skins.

The protein AIM2 (typically absent In Melanoma 2) is involved in inflammasome activation responsible for the development and maintenance of inflammatory skin diseases. Moreover, interleukin (IL)-18, a pleiotropic immune regulator, may play a role in the development and/or progression of inflammatory and autoimmune skin diseases. For example, IL-18 mediates signaling network in various dermatological diseases. Indeed, IL-18 plays a strong pro-inflammatory role by inducing interferon (IFN)-γ. But in skin diseases such as psoriasis, IL-18 induces Th1 and Th17 responses (with up regulation of the chemokine CXCL13 (C-X-C motif chemokine ligand 13), and in atopic dermatitis, IL-18 promotes Th-1 or Th-2 responses depending on cytokines milieu thus contributing to the release of cytokines such as IL-4, IL-13.

It is described that IL18RAP (interleukin 18 receptor accessory protein), can be involved in IL18-dependent signal transduction, leading to NF-kappa-B and JNK activation. Interleukin 26 (IL-26), a mediator of local immunity and inflammation, drives inflammation by enhancing the influx of neutrophils and stimulating the release of proinflammatory cytokines and chemokines from mature macrophages, monocytes, fibroblasts and epithelial cells. IL-26 is a driver and an effector of inflammation and is responsible for the sustained inflammation. In addition, it is demonstrated that IL-26 may be involved in chronic inflammatory disorders like inflammatory bowel disease, rheumatoid arthritis, or psoriasis.

In brief, it appears clear that the reinforcement or the preservation of the skin barrier function, the improvement of hydration, the prevention and/or the mitigation of aging and the prevention and/or alleviating the disorders and damages such as the inflammation within a skin, particularly within an already established compromised skin phenotype may be reached by acting at the different levels of the aforementioned skin barrier function players, namely from the SC's lipids components to the epidermis components and its renewal process.

*Bertholletia excelsa* is a plant belonging to the family Lecythidaceae having a large tree up to 50 meters high and two meters of diameter in average. It may grow in dry land and rain forests. It is available in dry land forests and can be used as an excellent species for reforestation of environmentally degraded areas. The fruit commonly called "Brazil nut" is basically a globular capsule with thick surface and dark-brown color. Each fruit contains in average between 10 to 25 seeds which are rich in oil due to its kernel, also called nut. Such oil is one of the well-known Brazilian oil seed and its production is of interest also in the social-economic organization of areas of wild harvesting in the North of Brazil and Amazon region. Usually, Brazil nuts are either consumed as a food ingredient and its shells are discarded or used for extracting its oil content from the seed by performing a well-known pressing process. The main compounds from the kernel of the seed of *Bertholletia excelsa* are, over total weight, oils (approximatively 60 to 70% by weight), particularly unsaturated fatty acids (oleic, linoleic and linolenic acids), proteins (approximatively 12 to 20%) and carbohydrates (approximatively 6 to 10%). Minor components are amino acids, polyphenols and minerals. Another notorious characteristic from the kernel is selenium content within the proteins.

Extracts from the bark of Brazil nut plants and Brazil nut seed oil-based extracts are known in cosmetic field. DE-A 102016009036 teaches a formulation comprising a blend of *Bertholletia excelsa* seed oil and hydrolyzed proteins from Brazil nut that may have activity on dry skin and dandruff. KR-B 101987421 teaches cosmetic compositions that comprise a mixture of plant extracts including *Bertholletia excelsa* seed oil. US-A 2014/090660 teaches a composition containing reducing sugars, proteins and/or amino acids from Brazil nut that may be used for hair care. WO 2009/082796 teaches cosmetic oil-in-water emulsions comprising plant oils of the genus Bactris and the genus *Bertholletia*. U.S. Pat. Nos. 6,471,972 and 7,887,858 mention various plant extracts and generally teach that various plant extracts may be able to stimulate collagen synthesis. EP-B 0809484, DE 69611082T2 and FR-B 2752527 teach compositions comprising an extract from bark or nut pericarp of *Bertholletia excelsa* that may stimulate collagen synthesis. It is also known that aqueous extract of the seed of *Bertholletia excelsa* is rich in selenium-proteins enabling to minimize the negative effect of hydrogen-peroxide levels by modulation of different oxidative-metabolic pathways. Ethanolic and hydroethanolic extracts of Brazil nut press cake containing polyphenols (gallic acid, protocatechuic acid, 2,4-dihydroxybenzoic acid, p-hydroxybenzoic acid, p-coumaric acid, and sinapic acid) at the range of 1.52 to 1.93 mg/GAE $g^{-1}$ of cake is known (Suellen G et al., Research Article, P2805-2814, 2015, DOI: 10.1002/jsfa.7448).

The aforementioned extracts from the bark of Brazil nut plants and Brazil nut seed oil-based extracts known in the art have several technical drawbacks. Often, the achieved cosmetic or pharmaceutical benefit effect is mainly due to either the oil content of the seeds or to the bark and the pericarp of the nut, which are rich in saponins. When using a bark extract of a *Bertholletia excelsa* tree, the tree is injured. The bark has been removed and the tree is of increased risk of pest influences such as fungal diseases. Furthermore, the bark is a very limited resource. On the other hand, seed oil is a valuable source for nutrition and specific cosmetic or pharmaceutical uses. Thus, there can be a competition of limited resources.

Therefore, there is still an unmet need for further extracts of *Bertholletia excelsa* that are well usable is cosmetic or pharmaceutical uses. It is desired that the extracts are based on sustainable resources. Thus, it is desired that the extracts do neither compete with nutrition and specific cosmetic or pharmaceutical uses and are, thus, not mainly seed-oil based, nor damage *Bertholletia excelsa* tree. Furthermore, it is desired that the extract is not seed oil-based and less fatty.

Surprisingly, it has been found that extracting an at least partly deoiled press residue of *Bertholletia excelsa* seeds with at least one alcoholic or hydroalcoholic solvent can lead to an extract having particularly good properties.

The present invention relates to an extract of *Bertholletia excelsa* seeds obtainable (or obtained) from extracting an at least partly deoiled press residue of *Bertholletia excelsa* seeds with at least one alcoholic or hydroalcoholic solvent.

A first aspect of the present invention relates to an extract of *Bertholletia excelsa* seeds obtainable (or obtained) from extracting an at least partly deoiled press residue of *Bertholletia excelsa* seeds having an oil content lower than the oil content in *Bertholletia excelsa* seeds before pressing with at least one alcoholic or hydroalcoholic solvent, wherein the extract comprises at least 1.5% by weight, referred to the total weight of the dry content of the extract, of one or more polyphenols, wherein the residual oil content is more than 15% and less than 50% by weight referred to the *Bertholletia excelsa* seeds before pressing.

Accordingly, the present invention also refers to a hydroalcoholic extract of an at least partly deoiled press residue of *Bertholletia excelsa* seeds comprising at least 1.5% by weight of one or more polyphenols, referred to the total weight of the dry content of the extract. The extract, both alcoholic and hydroalcoholic of the present invention has a special phytochemical profile. It may be likely that a certain amount of apolar polyphenols are extracted, with the oil, during the mechanical pressing.

An extract of the present invention is based on particularly sustainable resources. The at least partly deoiled press residue which is used as source of the present invention, is considered as a by-product. Usually, such at least partly deoiled press residue (also "seed cake") is used in the factory, is e.g. burned, or given back to the harvesting Brazilian communities for use as a fertilizer in agriculture or for their animal feeding. Therefore, using this source is particularly sustainable and is a circular economy positive approach that may enable valorizing a former by-product as a valuable component for new uses in cosmetic and/or pharmaceutical fields. The preparation of an extract of the present invention does neither compete with nutrition and specific cosmetic or pharmaceutical uses nor does it put any harm to *Bertholletia excelsa* trees.

Furthermore, it has been surprisingly found that the extract is not seed oil-based and less fatty. It has been further surprisingly found that compositions comprising (or even consisting of) at least one extract of the present invention may be used as an active ingredient for cosmetic and/or pharmaceutical purposes, in particular skin cosmetics. It may improve skin condition. It was surprisingly found that the extract of *Bertholletia excelsa* seeds of the present invention enables to exert beneficial effects in the skin. The experimental section of the present application demonstrates that the extract of the present invention may promote the skin's barrier function and/or skin hydration and/or may serve as a skin anti-aging agent and/or skin anti-inflammation agent and/or skin antipollution agent. It may upregulate the expression of the main genes and key proteins involved for accomplishing one or more of these functions.

Surprisingly, it has been found that an extract of the seed of *Bertholletia excelsa* can be used as an active ingredient, optionally for cosmetic uses. Thus, the present invention also refers to a composition comprising or consisting of at least one extract of the seed of *Bertholletia excelsa* for use as an active ingredient. The present invention further relates to the (optionally cosmetic) use of an extract the present invention as an active ingredient. The present invention also refers to a cosmetic skin and scalp method for treating or preventing the skin disorders and/or the skin damages in a subject, wherein the skin is administered with a sufficient amount of a composition comprising or consisting of at least one extract of the present invention (as an active ingredient) to said subject. The present application also refers to a method (cosmetic) for treating or preventing a disorder and/or damage in skin or scalp in a subject, wherein one or more parts or interest of the skin or scalp are administered with a sufficient amount of a composition of the present invention to said subject.

As used throughout the present invention, the extract of *Bertholletia excelsa* seeds of the present invention is also designated as "the extract" or by its abbreviation "EBE".

As used throughout the present invention, the terms "press residue", "press residual", "press rest", "seed cake" and "cake" may be understood interchangeably in the broadest sense as generally understood in the art. An at least partly deoiled press residue may be understood in the remaining mainly solid residuals remaining after pressing out the oil from the *Bertholletia excelsa* seeds. In other words, the at least partly deoiled press residue as used herein may preferably refer (essentially) to the compacted seeds obtained after removing, by mechanical pressing, its oil content. Examples of well-known means suitable for conducting the mechanical pressing are single or twin-screw extruders.

In a preferred embodiment, the at least partly deoiled press residue is a cold-press residue. Thus, the pressing may preferably be conducted in at least one pressing step that is conducted at a temperature of not more than 50° C., not more than 45° C., not more than 40° C., not more than 35° C., or not more than 30° C. In a preferred embodiment, pressing is conducted at ambient temperature, more preferably at a temperature of 18 to 25° C.

As used herein, the term "seed" as used herein refers to the seed comprising the kernel and the pericarp which is a brown thin layer surrounding the seed. As used herein, the terms "*Bertholletia excelsa* seed" and "Brazil nut seed" may be understood interchangeably in the broadest sense as generally understood in the art.

According to the present invention, the at least partly deoiled press residue is at least partly deoiled and, thus, has an oil content lower than the oil content in *Bertholletia excelsa* seeds before pressing. As used herein, the term "deoiled" may be understood in the broadest sense as generally understood in the art as a material (here: press residue of *Bertholletia excelsa* seeds) in which the oil content is reduced in comparison to the original material (here: *Bertholletia excelsa* seeds before pressing). Deoiling may be performed by mechanical pressing. The term "at least partly deoiled" maybe understood in the broadest sense in that the oil content is not necessarily reduced (essentially) completely, but to any degree below the content in the original material, i.e., oil is removed. The removed oil may be optionally recovered and may be optionally used for other purposes.

The oil content may be lower than before pressing by any degree. In a preferred embodiment, the at least partly deoiled press residue comprises an oil content that is at least 50% by weight lower than the oil content in the *Bertholletia excelsa* seeds before pressing. Preferably, at least 50% by weight of *Bertholletia excelsa* oil primarily comprised in the (fresh) *Bertholletia excelsa* seeds has been pressed out by means of pressing. The present invention also refers to an extract of *Bertholletia excelsa* seeds obtained from extracting an at least partly deoiled press residue of *Bertholletia excelsa* seeds with at least one alcoholic or hydroalcoholic solvent, wherein the at least partly deoiled press residue comprises an oil content that is at least 50% by weight lower than the oil content in the *Bertholletia excelsa* seeds before pressing. The residual oil content within the deoiled press residue may be typically determined by the well-known Soxhlet solvent extraction method consisting of mixing (an optionally determined amount of) deoiled press residue with an optionally determined amount of) apolar solvent (e.g., aliphatic hydrocarbon), evaporating the solvent during (optionally accurate) time and recovering the residual oil.

The at least partly deoiled press residue usable (or used) from which an extract of the present invention may be obtained may be any type of at least partly deoiled press residue of *Bertholletia excelsa* seeds. It may be obtained from a commercial supplier or may be prepared. It may be stored or may be freshly prepared. It may be prepared from stored *Bertholletia excelsa* seeds, dried *Bertholletia excelsa* seeds, frozen or freeze-dried *Bertholletia excelsa* seeds, or may be prepared from fresh *Bertholletia excelsa* seeds. In a preferred embodiment, the at least partly deoiled press residue is obtained from pressing fresh *Bertholletia excelsa* seeds. In a preferred embodiment, the at least partly deoiled press residue is fresh press residue.

As used herein, the term "extract" may be any substance made by extracting a part of at least partly deoiled press residue of *Bertholletia excelsa* seed. In accordance with the present invention, the extract of at least partly deoiled press residue of *Bertholletia excelsa* seed may be a solvent-based extract obtainable/obtained by solvent extraction of the said plant. As used herein, extracting is achieved by using at least one solvent. Accordingly, in a preferred embodiment, the extract is obtained by performing a solvent extraction method. In a preferred embodiment, the extract is obtained from alcoholic or hydroalcoholic extraction methods including cold or hot extraction, ultrasonic extraction, reflux cooling, needle extraction and microwaves extraction. Herein, before the solvent extraction step, a preparation step may optionally be performed such as a decontamination step of the at least partly deoiled press residue by using known appropriate means in the field such as heat. The solvent may be added to the deoiled press residue. In a further step, the solid parts of the deoiled press residue may optionally be separated by the primary extract. This may be achieved by any means known in the field such as, e.g., filtration, sieving, ultrafiltration, cross-flow filtration, centrifugation, precipitation over time, or a combination of two or more thereof.

As used herein, the term "fresh seed" or "fresh press residue" may be understood in the broadest sense in the art. As used herein, fresh seeds are preferably those which were neither (significantly) dried (i.e., losing more than 19%, more than 20% or more than 50% of their original water content upon harvesting the seeds) nor frozen or freeze-dried. Preferably, fresh seeds have not been stored for more than one month, more than three weeks, more than two weeks, or more than one week. As used herein, fresh at least partly deoiled press residue is preferably such which was neither (significantly) dried (i.e., losing more than 19%, more than 20% or more than 50% of their original water content upon pressing the seeds) nor frozen or freeze-dried. Preferably, at least partly deoiled press residue has not been stored for more than one month, more than three weeks, more than two weeks, or more than one week. Indeed, in fresh seeds, native compounds, particularly sensitive oxidable components may be conserved in the seed before the extraction process is performed. The at least partly deoiled press residue may be used in any form such as, e.g., as powder, crushed, pellets, granular or any block form.

The extract according to the present invention may be obtained by any means. It may optionally be obtained by a commercial supplier or may be partly or completely prepared from the at least partly deoiled press residue of *Bertholletia excelsa* seeds.

The alcoholic or hydroalcoholic solvent may be any solvent or solvent mixture that comprises at least on alcohol. Preferably, the alcoholic or hydroalcoholic solvent is a solvent or solvent mixture that is mainly composed of one or more alcohols and water. Preferably, the alcoholic or hydroalcoholic solvent is a solvent or solvent mixture that is composed of more than 50% by weight, at least 60% by weight, at least 70% by weight, at least 80% by weight, at least 90% by weight, at least 95% by weight, consists (essentially) of one or more alcohols and water. Optionally, the alcoholic or hydroalcoholic solvent is a solvent or solvent mixture that is composed of more than 50% by weight, at least 60% by weight, at least 70% by weight, at least 80% by weight, at least 90% by weight, at least 95% by weight, consists (essentially) of one or more alcohols. As used herein, water may also include hot water or subcritical water. Also one or more aqueous buffers may be used.

As used herein, the term "hydroalcoholic" may be understood in the broadest sense as generally understood in the art. It may be any composition comprising alcohol and water. A hydroalcoholic solvent may be any alcohol/water mixture. In a preferred embodiment, the solvent is an alcohol/water mixture containing between and 90% (v/v) alcohol, or containing between 25 and 85% (v/v) alcohol, or containing between 50 and 82% (v/v) alcohol, or containing between 60 and 80% (v/v) alcohol, or containing between 65 and 75% (v/v) alcohol, or containing approximately 70% (v/v) alcohol.

In a preferred embodiment, the at least one alcoholic or hydroalcoholic solvent is selected from the group consisting of ethanol, methanol, propanol, butanol, pentanol, phenol, glycerol, 1,3-butylene glycol, propane diol, and mixtures of two or more thereof and mixtures of one or more thereof with water or an aqueous buffer.

In a preferred embodiment, the at least one alcoholic or hydroalcoholic solvent is ethanol, a mixture of ethanol and water, or a mixture of ethanol and an aqueous buffer.

In this context, an alcohol may be any alcohol or alcohol mixture, in particular an alcohol selected from the group consisting of ethanol, methanol or a mixture thereof.

In a preferred embodiment, a hydroalcoholic solvent may be a hydroethanolic solvent. Thus, in a preferred embodiment, the solvent is an ethanol/water mixture containing between 10 and 90% (v/v) ethanol, or containing between 25 and 85% (v/v) ethanol, or containing between 50 and 82% (v/v) ethanol, or containing between 60 and 80% (v/v) ethanol, or containing between 65 and 75% (v/v) ethanol, or containing approximately 70% (v/v) ethanol. In another preferred embodiment, a hydroalcoholic solvent may be a hydromethanolic solvent.

In a further preferred embodiment, the extract of the present invention is a hydroethanolic or an ethanolic extract, i.e., is the solvent an ethanolic or a hydroethanoloic solvent. In a preferred embodiment, the extract of the present invention is a hydroethanolic extract, i.e., is the solvent a hydroethanoloic solvent. In a preferred embodiment, the at least one extract of the present invention is a hydroethanolic extract obtained by extraction with an ethanol/water mixture containing between 10 and 90% (v/v) ethanol, or containing between 25 and 85% (v/v) ethanol, or containing between 50 and 82% (v/v) ethanol, or containing between 60 and 80% (v/v) ethanol, or containing between 65 and 75% (v/v) ethanol, or containing approximately 70% (v/v) ethanol.

In a preferred embodiment, the extract of the present invention contains one or more polyphenols. The extract may contain one or more polyphenols in any content range. In a preferred embodiment, the extract comprises at least 1.8% by weight, more preferably at least 2% by weight, in particular 3% by weight, referred to the total weight of the dry content of the extract, of one or more polyphenols.

The quantification of the total polyphenols may be conducted by any means. In a preferred embodiment, the quantification of the total polyphenols content of the extract of the present invention may be performed according to the known Folin-Ciocalteu method. This analytical method may be based on spectrometric measure. Typically, all the polyphenols content in the extract of the invention is oxidized by the Folin-Ciocalteu reagents. These reagents may comprise of a mixture of phosphotungstic and phosphomolybdic acid which is reduced, during the oxidation of phenolic substances, to a mixture of blue oxides of tungsten and molybdenum. The blue coloration produced may have a maximum absorption at around 750 to 760 nm, which is typically proportional to the amount of the oxidised phenolic components.

In a preferred embodiment, the extract is a hydroalcoholic or alcoholic, in particular a hydroethanolic or ethanolic, extract that comprises at least 1.5% by weight, preferably at least 1.8% by weight, particularly at least 2% by weight, referred to the total weight of the dry content of the extract, of one or more polyphenols.

As noted above, the at least partly deoiled press residue comprises an oil content that is at least 50% by weight lower than the oil content in the *Bertholletia excelsa* seeds before pressing. In a preferred embodiment, the at least partly deoiled press residue comprises a residual oil content more than 15 to 45% by weight, preferably 20 to 45% by weight, more preferably 20 to 40% by weight, in particular to 20 to 35% by weight, referred to the *Bertholletia excelsa* seeds before pressing.

In a preferred embodiment, the extract is a hydroalcoholic or alcoholic, in particular a hydroethanolic or ethanolic, extract that comprises at least 1.8% by weight, more preferably at least 2% by weight, in particular 3% by weight, referred to the total weight of the dry content of the extract, of one or more polyphenols and that is obtainable (or obtained) from extracting an at least partly deoiled press residue that comprises a residual oil content more than 15 to 45% by weight, preferably 20 to 45% by weight, more preferably 20 to 40% by weight, in particular to 20 to 35% by weight, referred to the *Bertholletia excelsa* seeds before pressing.

In a preferred embodiment, the solids content (also: "dry matter content") in the extract may represent at least 0.1% by weight, preferably at least 0.5% by weight, more preferably at least 1% by weight, even more preferably at least 1.5% by weight (or even at least 2% by weight), referred to the total weight of the extract. The solids content is measured by known methods, for example by passing an oven at 105° C. in the presence of a sand of a sample of given initial weight until a constant weight is obtained.

In another embodiment, the dry content of the extract may represent at least 10 g/L (weight/volume of solvent), preferably at least 15 g/L (weight/volume of solvent), even more preferably at least 20 g/L (weight/volume of solvent). Also in this context, the solids content may be measured by passing the oven at 105° C. in the presence of a sand of a sample of given initial weight until a constant weight is obtained. As used in this context, the solvent may be considered as the evaporable liquids (evaporable at a temperature of 105° C.) and the volume is preferably its volume at ambient temperature and ambient pressure (e.g., (approximately) 20° C. and (approximately) 1013 mbar). In other words the solids content of the extract is at least 10 g/L, at least 15 g/L, or at least 20 g/L, based on the solid residual when the components which are evaporable at 105° C. at ambient pressure have been removed, referred to the volume of the condensed evaporable components at room temperature and ambient temperature.

Extracting may be performed at any temperature suitable for this purpose. Preferably, extraction is conducted at a temperature in the range of 10 to 150° C., or 15 to 100° C., or 20 to 80° C., or 25 to 70° C. or 15 to 25° C., or approximately 20° C. In a preferred embodiment, extraction is conducted at ambient temperature (i.e., 15 to 25° C., in particular approximately 20° C.). In a preferred embodiment, extracting is conducted at ambient temperature (i.e., 15 to 25° C., in particular approximately 20° C.) and ambient pressure (i.e., 980 to 1200 hPa). In a preferred embodiment, extraction is conducted at ambient temperature (i.e., 15 to 25° C., in particular approximately 20° C.) and ambient pressure (i.e., 980 to 1200 hPa) using an ethanol/water mixture containing between 65 and 75% (v/v) ethanol, in particular approximately 70% (v/v) ethanol.

Extracting may be conducted for any time interval suitable for this purpose. For example, the extraction may be conducted for a time interval in the range of less than 20 min, of 30 min to 1 hour, of 1 hour to 2 hours, of 90 min to 6 hours, of 2 hours to 24 hours, of 6 hours to 36 hours, of 12 hours to two days, of one day to a week. In a preferred embodiment, extraction may be conducted (preferably at ambient temperature of 15 to 25° C.) for a time interval in the range of 20 min to 48 hours, of 25 min to three days, exemplarily approximately between 25 min and 24 hours, between 25 min and 10 hours, or between 30 min and 5 hours. It may be conducted over night.

The extract according to the present invention may be liquid, pasty or solid at standard conditions (room temperature of approximately 20° C., normal pressure of approximately 1013 hPa). In this context, the terms "liquid" and "fluid" may be understood interchangeably. Preferably, the extract is first obtained in liquid form. Then, the one or more solvents may optionally be removed to obtain a solid form of the extract. A liquid extract can also be concentrated. Then, preferably, parts of the one or more solvents are removed. Optionally, a liquid or pasty extract may be obtained. Optionally, the extract may also be diluted with one or more solvents for obtaining a solvent-based extract. Optionally, the extract may also be purified by any means (e.g., crystallization, chromatographic means, etc.). An extract may be optionally designated as "tincture" or "absolute". The solvent used for the preparation of the solvent-based extract may be an aqueous solvent (water or a buffer), or it may be a combination of an aqueous solvent and a liquid organic solvent. Accordingly, the extract of the at least partly deoiled press residue of *Bertholletia excelsa* seeds according to the present invention is a solvent-based extract wherein the dilution solvent may be selected from water, aqueous buffer, alcohols, glycols, ethyl lactate, isopropyl myristate, triglycerides, tri-ethyl citrate, dicaprylyl ether, glyceryl isostearate, glyceryl stearate, ethyl acetate or a mixture thereof. The alcohols may be preferably selected from methanol and ethanol. Glycols may be preferably selected from pentylene glycol and glycerol. The extract of the at least partly deoiled press residue of *Bertholletia excelsa* seeds may be a mixture of glycerol:water in a volume ratio from 95/5 to 5/95, preferably from 80/20 to 20/80.

The at least one extract of the seed, preferably of the at least partly deoiled press residue of *Bertholletia excelsa* seeds may be optionally obtained in a fraction produced by conducting other purification methods including separation through an ultrafiltration membrane with a constant molecular weight cut-off value, or separation through various chromatographic methods, or liquid-liquid separation or crystallization or precipitation.

For example, an extract of the seed, preferably of the deoiled press residue may be prepared by drying the seed or the deoiled press residue of *Bertholletia excelsa* seeds, preferably the fresh material, and then extracting it with solvent, particularly with alcoholic or hydrated alcoholic, optionally followed by filtration under reduced pressure and ended by concentration by solvent evaporation.

As used herein, the term "dry extract" may be understood in the broadest sense as an extract according to the present invention as dry matter, i.e., without the solvent. The dry extract may optionally be physically present as dry matter. It will, however, be directly understood that, in calculations referring a percentage referred to dry matter, it does not have to be dry matter present in physical form, but the dry extract may also be present in dissolved form. Then, in the calculation, the mass of the solvent is mathematically subtracted from the total mass.

In a preferred embodiment of the present invention, the at least partly deoiled press residue is a dried press residue, preferably a dried press residue from which water has been partly or completely removed.

Optionally, the at least one solvent used for extracting may be partly or completely removed by evaporation.

Dry matter (in physical form) may be obtained by a suitable extraction method, followed by a step of drying the extract obtained. The drying may be performed by any method suitable for this purpose known in the art. Drying means removing the one or more solvents used for extraction. Removing the one or more solvents may be performed by any means. For example, it may be achieved by subjecting the extract to a hot and dry atmosphere and/or placing the extract on a heated plate in order to evaporate the solvent. For example, drying may be achieved by evaporation in a vacuum and/or at elevated temperature (e.g., in a rotary (vacuum) evaporator) or by crystallization of the solid material of interest. Alternatively, or additionally, drying may be achieved by out by atomisation or by lyophilization.

The present invention also relates to means for preparing the extract of *Bertholletia excelsa* seeds of the present invention. Accordingly, a further aspect of the present invention relates to a method for preparing an extract of *Bertholletia excelsa* seeds comprising the following successive steps:

(i) providing an at least partly deoiled press residue of *Bertholletia excelsa* seeds, preferably from fresh seeds, comprising a residual oil content more than 15% and less than 50% by weight referred to the *Bertholletia excelsa* seeds before pressing, wherein the at least partly deoiled press residue is optionally dried;

(ii) contacting the deoiled press residue with at least one alcoholic or hydroalcoholic solvent for 30 minutes to 2 hours, at 15 to 30° C., preferably at 18 to 25° C.;

(iii) enabling homogenization of the deoiled press residue within the at least one alcoholic or hydroalcoholic solvent;

(iv) separating the extract from the solid residuals of step (iii), preferably by means of filtration or centrifugation; and (v) concentrating the extract by removing the at least one solvent or parts thereof.

In a preferred embodiment, concentrating the extract may be performed between 2 and 5 times.

It will be understood that the definitions and preferred embodiments made in the context of the extract of the present invention mutatis mutandis apply to the method for preparing an extract of *Bertholletia excelsa* seeds.

Accordingly, the present invention also refers to an extract obtainable (or obtained) from a method of the present invention. In a preferred embodiment, the extract obtainable (or obtained) from a method of the present invention is characterized as defined above.

An extract of *Bertholletia excelsa* seeds may be used as active component. An extract of *Bertholletia excelsa* seeds may be used as such in pure form or may be mixed with one or more other components. In other words, it may be used as active ingredient in a composition. Preferably, it is used in a cosmetic or pharmaceutic composition. Accordingly, a further aspect of the present invention relates to a cosmetic or pharmaceutic composition comprising:

(A) at least one extract of *Bertholletia excelsa* seeds of the present invention as an active ingredient; and (B) at least one further cosmetically and/or pharmaceutically acceptable ingredient other than the extract of *Bertholletia excelsa* seeds.

It will be understood that the definitions and preferred embodiments made in the context of the extract of the present invention mutatis mutandis apply to a composition comprising such extract of *Bertholletia excelsa* seeds.

Herein, the at least one extract of *Bertholletia excelsa* seeds may optionally be considered as an (or optionally even the sole) active ingredient. The term "active ingredient" may be understood in the broadest sense as a component that may exhibit a desired and intended activity, either alone or together with one or more other ingredients such as one or more carriers that are themselves inactive or other active ingredient that may optionally act synergistically. Preferably, the active ingredient of the present invention is a cosmetically active ingredient.

The cosmetic or pharmaceutic composition may be used for any purpose and in any form. In a preferred embodiment, the composition is a composition for topic use selected from the group consisting of a solution, a suspension, an emulsion, a cream, a paste, a gel, a lotion, a powder, a soap, a surfactant-containing water, an oil, a shampooing, and a spray, or wherein the composition is a nutraceutical composition which is administered orally.

The composition may also be or may be comprised in a product selected from the group consisting of emulsions, gels, ointments, tonics, liquid soaps, bar soaps, bath oils, shower oils, massage oils, makeups, scalp treatments, aftershaves, shaving products, deodorants, shower gel, shampoos, and combinations of two or more thereof.

Optionally a cosmetic or pharmaceutical composition may also be a nutraceutical composition which can be administered orally to a subject. Then, the cosmetic or pharmaceutical composition may optionally be included in a food product, such as a food supplement. Then, the composition may typically have a systemic effect. A nutraceutical composition according to the present invention may be formulated, with acceptable carriers, in any form suitable for oral administration such as, e.g., tablets, capsules, granules, powder, solution, emulsion, or suspension.

The cosmetic or pharmaceutic composition may contain the extract of *Bertholletia excelsa* seeds of the present invention may be comprised in any content. In a preferred embodiment, the composition comprises less than 30% by weight, referred to the total weight of the composition, of the at least one extract of *Bertholletia excelsa* seeds. In a preferred embodiment, the composition comprises 0.0001 to 20% by weight, more preferably 0.001 to 15% by weight, even more preferably 0.005 to 10% by weight, in particular 0.01 to 5% by weight, referred to the total weight of the composition, of the at least one extract of *Bertholletia excelsa* seeds.

The at least one further cosmetically and/or pharmaceutically acceptable ingredient other than the extract of *Bertholletia excelsa* seeds may be any cosmetically and/or pharmaceutically acceptable ingredient. In a preferred embodiment, the cosmetically and/or pharmaceutically acceptable ingredient is or comprises at least one cosmetically and/or pharmaceutically acceptable carrier.

As used herein, the terms "pharmaceutically acceptable carrier", "pharmaceutically acceptable excipient", "cosmetically acceptable carrier", "cosmetically acceptable excipient", "carrier" and "excipient" may be understood interchangeably in the broadest sense as any substance that may support the cosmetic and/or pharmacological acceptance or usability of the composition according to the present invention containing the extract of *Bertholletia excelsa* seeds. Preferably, neither the extract of *Bertholletia excelsa* seeds nor a composition containing such at least one extract according to the present invention is toxic when applied to the tissue.

The composition ready to use preferably may be a liquid formulation, in peculiar a composition suitable for topic and oral administration. The storage form of the composition may also be liquid, but may also be a dried form (e.g. a powder such as a powder comprising or consisting of the at least one extract of *Bertholletia excelsa* seeds or may be a paste or syrup or the like. Optionally, a dried form, paste or syrup may be dissolved or emulsified prior to being administered to the skin of interest.

A cosmetically and/or pharmaceutically acceptable carrier may exemplarily be selected from the list consisting of an aqueous buffer, saline, water, alcohols, vegetable oils, mineral oils, polymers, or combination of two or more thereof. Optionally, a cosmetically and/or pharmaceutically acceptable carrier may contain one or more cosmetically and/or pharmaceutically acceptable additives. In a preferred embodiment, such cosmetically and/or pharmaceutically acceptable additives may be selected from the group consisting of fragrances/perfumes, dyes, pigments, emulsifiers, lubricants, chelating agents, acidity regulators, antimicrobial agents, preservatives, antioxidants, and combinations of two or more thereof. For instance, the cosmetically and/or pharmaceutically acceptable carrier may optionally contain one or more detergents, triethanolamine, one or more fragrances, one or more foaming agents (e.g., sodium lauryl sulphate (SLS), sodium docecyl sulphate (SDS)), one or more colouring agents (e.g., food colouring, pigments), one or more vitamins, one or more salts (e.g., sodium, potassium, calcium, zinc salts), one or more humectants (e.g., sorbitol, glycerol, butylene glycol, propylene glycol, mannitol, propylene glycol, polydextrose), one or more enzymes, one or more preserving agents (e.g., benzoic acid, methylparaben, one or more antioxidants, one or more herbal and plant extracts, one or more stabilizing agents, one or more chelating agents (e.g., ethylenediaminetetraacetic acid (EDTA), one or more polymers (e.g., carboxyvinyl polymer, carboxymethyl cellulose, cellulose, carboxyethyl cellulose), one or more stabilizers, one or more solubilizers, one or more emollients, and/or one or more uptake mediators (e.g., polyethylene imine (PEI), a cell-penetrating peptide (CPP), a protein transduction domain (PTD), an antimicrobial peptide, etc.). Moreover, the composition of the present invention may contain, in addition to the at least one extract of *Bertholletia excelsa* seeds one or more other active ingredients, working either synergistically and/or complementarily with the said extract of *Bertholletia excelsa* seeds without affecting its activity or its indented use as mentioned above.

The composition according to the present invention may be cosmetic product or may be comprised in a cosmetic product. Deleterious effects in the skin may be reduced or avoided, according to the safety studies and legal requirements. The composition may be for any use. Any administration routes are suitable that lead to the desired purpose as claimed. Administration may be local or systemic administration. Preferably, administration is local administration. Administration may be topic administration, transdermal administration, oral administration, administration by mean of injection (e.g., intravenous (i.v.), intraarterial (i.a.), intraperitoneal (i.p.), intramuscular (i.m.), and subcutaneous (s.c.) injection), or nasal administration. For example, the composition according to the present invention may be formulated, with acceptable carriers in any suitable form for topical, oral, rectal, transmucosal, transnasal, intestinal, enteral and parenteral administrations.

In a preferred embodiment, the composition is a composition for topic use. In a preferred embodiment, the composition is a composition for topic use which is administered topically to a subject. In other words, the composition according to the present invention may be administered topically. In a preferred embodiment, the composition is a composition for topic use which is administered topically to a part of the skin such as, e.g., to the face, scalp, or part of a body. Skin may be all types of skin, including compromised skin, dry skin, healthy skin, normal skin and oily skin.

As indicated above, the extract of *Bertholletia excelsa* seeds or the composition of the present invention may be used for any purpose. Preferably, it is used for a cosmetic and/or pharmaceutical purpose.

Surprisingly, it was found that the extract of *Bertholletia excelsa* seeds and the composition of the present invention enable treating, regulating and/or preventing dysfunctions of the epidermal barrier function leading to many disorders and damages of the skin.

Accordingly, in a further aspect, the present invention relates to the use of an extract of *Bertholletia excelsa* seeds or a cosmetic or pharmaceutic composition of the present invention for reinforcing, for preserving and/or for restoring the skin barrier function, for improving the skin hydration, for preventing and/or mitigating skin aging, and/or for alleviating and/or for preventing skin disorders or damages.

It will be understood that the definitions and preferred embodiments made in the context of the extract of *Bertholletia excelsa* seeds or a composition comprising such extract of the present invention mutatis mutandis apply to the use thereof.

The present invention also relates to an extract of *Bertholletia excelsa* seeds or a cosmetic or pharmaceutic composition of the present invention for use as a medicament. The present invention also relates to an extract of *Bertholletia excelsa* seeds or a cosmetic or pharmaceutic composition of the present invention for use in a method for treating or preventing a skin disorder and/or a skin damage. In a preferred embodiment, it is for reinforcing, for preserving and/or for restoring the skin barrier function, for improving the skin hydration, for preventing and/or mitigating skin aging, and/or for alleviating and/or for preventing skin disorders or damages.

As used herein, the term "disorder" may be understood in the broadest sense as any pathological condition. It may optionally be an inherent or an acquired disease. As used herein, the term "damage" may be understood in the broadest sense as any perturbation or dysfunction in a tissue, particularly in (otherwise) healthy tissue. As used herein, disorders and damages may be induced by both internal and external aggressions such as aging, one or more genetic factors, one or more hormones, light exposure (e.g., exposure to ultra-violet (UV) light, exposure visible light and/or exposure to infra-red (IR) light), exposure to particular pollution, exposure to one or more pathogens (including natural and chemicals products) and/or allergens, exposure to fluctuating temperature and/or humidity, and/or exposure to mechanical constraints (including such due to daily habits such as shaving, gloves, and/or wearing masks).

The extract of *Bertholletia excelsa* seeds or a composition comprising such of the present invention may have a local and/or a systemic effect. In a preferred embodiment, when administered locally and/or topically, it (mainly or completely) has a local effect.

In a preferred embodiment, the use is for tissue care, preferably wherein the use is for ameliorating the tissue condition selected from the group consisting of dryness, redness, aberrant pigmentation and sebum-deregulation, itching and inflammation, atopic dermatitis, psoriasis, vitiligo, systemic lupus erythematosus, ichthyosis, and skin aging.

The tissue treated may be any tissue. In a preferred embodiment, the tissue is selected from a group consisting of a tissue present in the skin and in the scalp, in particular a dermal tissue, an epidermal tissue, a subcutaneous tissue, and a combination of two or more thereof.

The skin treated may be any type of skin. The extract of *Bertholletia excelsa* seeds of the present invention may be an active ingredient for improving the conditions of any type of skin. In a preferred embodiment, the skin is selected from compromised skin, dry skin, healthy skin, normal skin and oily skin.

In a preferred embodiment, the use is for:

(a) stimulating skin lipids metabolism, preferably cholesterol, fatty acids, sphingolipids and/or ceramides metabolism;

(b) promoting epidermal proliferation and/or epidermal differentiation;

(c) regulating keratinocytes cohesion and/or cell cytoskeleton; and/or (d) regulating inflammatory processes by inhibiting the activation of the inflammasome and the proinflammatory molecules.

Stimulating skin lipids metabolism may optionally also be stimulating of the global skin lipids content, preferably the cholesterol, the fatty acids, the sphingolipids and the ceramides.

Reinforcing or preserving skin barrier function by optionally acting at different levels of skin barrier (keratinocytes differentiation process, cytoskeleton, keratinocytes cohesion thanks to TJs and lipids metabolism) improve the skin conditions globally. It may also optionally mitigate the processes leading to compromised skins. Indeed, such reinforcement may optionally prevent the entry of harmful substances into the body through the defective skin barrier and may optionally prevent water loss.

As used therein, the terms "compromised skin" and "compromised skin phenotype" may be understood in a broad sense as any type of skin that is exposed to one or more harmful or irritating influences.

A subject having the tissue of interest, in particular skin, may be suffering from or may be of risk of developing a disorder as laid out above.

As used in the context of the present invention, the term "subject" may be understood in the broadest sense as any living being. A subject preferably is a human or animal, more preferably a human or mammal, in particular a human being.

The term "suffering from" as used herein may be understood in the broadest sense in that the subject has developed a pathological condition. The subject suffering from a disorder does not necessarily, but may optionally, bear one or more medicinal symptoms. The term "being at risk of" or "being at risk of developing" may be understood in the broadest sense in that the subject has a certain risk of having a disorder in the sense of the present invention.

Another aspect of the invention relates to an extract of *Bertholletia excelsa* seeds obtainable from extracting at least a partly deoiled press residue of *Bertholletia excelsa* seeds having a residual oil content of 0 to 50% by weight than the oil content in *Bertholletia excelsa* seeds before pressing with at least one alcoholic or hydroalcoholic solvent, wherein the extract comprises at least 1.5% by weight, preferably at least 1.8% by weight, more preferably at least 2% by weight, in particular at least 3% by weight, referred to the total weight of the dry content of the extract, of one or more polyphenols, for reinforcing, for preserving and/or for restoring the skin barrier function, for improving the skin hydration, for preventing and/or mitigating skin aging, and/or for alleviating and/or for preventing skin disorders or damages.

Throughout this specification and the claims, unless the context requires otherwise, the open-worded terms such as "comprise", "contain", "include", etc., and variations such as "comprises", "contains", "includes", "comprising", "containing", "including", etc., maybe understood to imply the inclusion of a stated component, member, integer or step or group of components, members, integers or steps, but not the exclusion of any other components.

The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually as well as in combination with each other recited herein. All methods and procedural steps, including product-by-process steps described herein can be performed in any suitable order unless otherwise indicated herein or otherwise clearly contradicted by context. The use of any and all examples, or exemplary language (e.g., "such as", "for example"), provided herein is intended merely to better illustrate the invention and does not pose a limitation on the scope of the invention otherwise claimed. No language in the specification should be construed as indicating any non-claimed element essential to the practice of the invention.

It should be understood that the aspects and embodiments may be combined in any manner and in any number to additional embodiments. Any permutations and combinations of all described elements in this application should be considered disclosed by the description of the present application unless the context indicates otherwise.

Unless defined otherwise, all technical and scientific terms used herein have the same meaning as commonly understood by a person skilled in the art. Although the methods and materials described herein are preferred, other methods and materials similar or equivalent to those described herein can be used in the practice or testing of the present invention as well.

All documents cited or referenced herein are hereby incorporated by reference and may be employed in the practice of the invention. More specifically, all referenced documents are incorporated by reference to the same extent as if each individual document was specifically and individually indicated to be incorporated by reference.

The following Examples and Figures are intended to illustrate further embodiments of the present invention without limiting its scope.

EXAMPLES

Figure 1A:
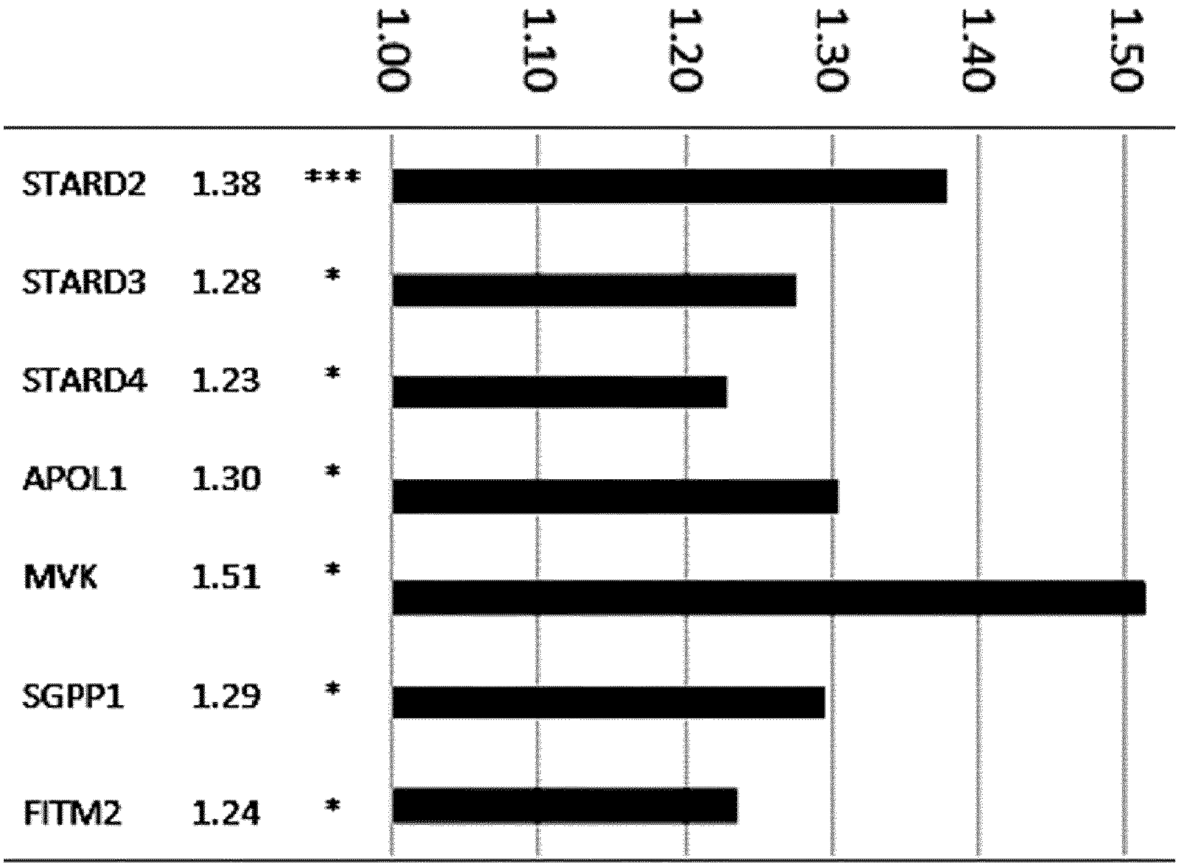
FIG. 1 (A, B) demonstrates the modulation of epidermal lipids genes and proteins expressions of the reconstructed human skin models treated with an extract of *Bertholletia excelsa* seeds ("seed cake"). The set of cellular factors depicted in FIG. 1A comprises STARD2 (StAR-related lipid transfer protein 2), STARD3 (StAR-related lipid transfer protein 3), STARD4 (StAR-related lipid transfer protein 4), APOL1 (apolipoprotein L1), MVK (mevalonate kinase), SGPP1 (sphingosine-1-phosphate phosphatase 1), and FITM2 (fat-inducing protein 2). The set of cellular factors depicted in FIG. 1B comprises DHCR7 (7-dehydrocholesterol reductase), CPT2 (carnitine O-palmitoyltransferase 2), ACOT11 (acyl-coenzyme A thioesterase 11), and TECR (very-long-chain enoyl-CoA reductase).

1 Preparation of Extract of the at Least Partly Deoiled Press Residue ("Seed Cake") of *Bertholletia excelsa*

The seeds of *Bertholletia excelsa* were harvested. Two days later, the seeds were pressed for recovering the majority of their oil content. The obtained press residues contained up to 30% by weight of oil. Prior to the extraction, the press deoiled residues were decontaminated by heating for obtaining dried press deoiled residues reduced in number of bacteria, mold and yeasts.

a. Extraction Step:

Extraction was conducted on the dried and decontaminated at least partly deoiled press residue (hereinafter "press residue") as defined above. Approximately 40 kg of each press residues were used.

Extraction was performed by using solvent extractor according to a standard procedure. For example, extraction was conducted by the means of 70% (v/v) ethanol in water (i.e., ethanol/water ratio of 70:30, (v/v)). The extraction was performed by means of complete homogenization of the at least partly deoiled press residue within the extractor solvent and constant stirring (maximum 500 rpm) during 1 hour at ambient temperature (i.e., 18 to 25° C.).

b. Filtration Step:

Subsequently, the obtained hydroethanolic extract was filtered according to a standard procedure. For example, filtration was conducted by using filters with increased pores, starting from tissue having pore diameter from 3 to 10 μm to avoid microbial contamination. The obtained filtered liquid was limpid and had less than 10 CFU/g (colony forming unit per gram) of bacteria and less than 10 CFU/g of mold and yeast.

c. Concentration Step:

The filtered liquid extract obtained in step b) was further concentrated according a standard procedure. For example, concentration was performed with reduced pressure in a constant vacuum, in a continuous stirring at temperature between 50 to 80° C., until complete evaporation of ethanol for obtaining a concentrate, having acceptable microbial content, which preferably constitutes the extract according to the present invention. The total polyphenols content of the said concentrated extract obtained, measured according to the Folin-Ciocalteu method, represented 3% by weight, based on the total weight of the dry extract. For the following, the extract of the at least partly deoiled press residue of *Bertholletia excelsa* of the present invention obtained at the end the step c) is diluted in a mixture of glycerol:water 80/20 (v/v) and will be called "EBE", it has a dry content of 20 g per 1 L of glycerol:water.

The EBE does not contain in terms of polyphenol components the gallic acid, protocatechuic acid, 2,4-dihydroxybenzoic acid, p-hydroxybenzoic acid, p-coumaric acid, catechin and sinapic acid.

2. In Vitro Studies

In the following studies, the skin barrier function improvement, the skin hydration effect and the skin anti-inflammatory effect of EBE were demonstrated.

a. EBE Stimulates Lipids Metabolism and Results in a Global Upregulation of Genes Expressions Involved in Skin Lipids Metabolism The stimulatory effect of EBE on lipids metabolism was assessed in vitro by means of a 3D full thickness reconstructed human skin model FTS (Phenion, Henkel). Briefly summarized, EBE formulated at 0.25% by weight or the placebo as described in Table 1, were topically applied at 2 $mg/cm^2$ on full thickness reconstructed human skin cultured for 24 h and five days at 37° C. with 5% $CO_2$.

TABLE 1

Gel cream containing EBE at 0.25% by weight, and placebo

| Composition of gel cream in (% weight) | Placebo | EBE at 0.25% by weight |
|---|---|---|
| Water | 96.00 | 95.75 |
| Ammonium acryloyldimethyltaurate/VP crosspolymer | 0.80 | 0.80 |
| Dicaprylyl ether | 1.00 | 1.00 |
| Aqueous buffer of citric acid and sodium citrate | 1.00 | 1.00 |
| EBE | 0.00 | 0.25 |
| Phenoxyethanol and methylparaben and ethylparaben | 1.10 | 1.10 |
| Fragrance | 0.10 | 0.10 |

After 24 hours of tissue culture, total RNAs were extracted using RNeasy Mini kit from Qiagen. Their concentrations and integrities were analysed by spectrophotometry and capillary electrophoresis. Transcriptomic analysis was performed on Affymetrix human Clariom S arrays according to the Affymetrix user manual.

After five days of culture, three tissues per conditions were sampled for proteomic analysis and three other tissues per conditions were sampled for histologic analyses. Proteins were extracted using a lysis buffer. Protein concentrations were determined using the Bradford method and quality control of the extraction was validated by high resolution SDS-PAGE. Mass spectrometry (MS) analysis were performed on a Dionex U3000 RSLC nano-LC system coupled to an Orbitrap Fusion mass spectrometer (Thermo Fisher Scientific). For histology, tissues were divided in two parts: one half were snap-frozen, and the other half were paraffin embedded.

To analyse data from transcriptomic and proteomic studies, all significantly deregulated genes were analysed using the DAVID bioinformatics resources. The tool identifies functional regulated pathways from large genes or proteins datasets. This analysis showed an enrichment of transcripts involved in lipids metabolism pathway.

Results:

The FIG. 1 shows upregulation of genes due to EBE, analysed by Affymetrix technology on FTS models treated with 0.25% by weight of EBE compared to a placebo. All analyses were performed in triplicate. Lipids metabolism was highlighted by DAVID bioinformatics resources as modulated functional pathway, and the list of significantly modulated genes involved in was displayed. Statistical analyses were performed in comparison to the placebo.

As shown in FIG. 1A, an upregulation of the transcription of genes involved in cholesterol metabolism and its transport (MVK, STARD3, STARD4), ceramides metabolism via activation of sphingolipids pathway (SGPP1), phosphatidylcholine metabolism and transport (STARD2), lipids storage and their transports (FITM2 and APOL1) were demonstrated in the cells tissues treated by EBE. StarD family of proteins that have steroidogenic acute regulatory protein-related lipid transfer domains and function in the transport and metabolism of lipids. StarD3 and 4 are involved in cholesterol and sterols transport.

Figure 1B:
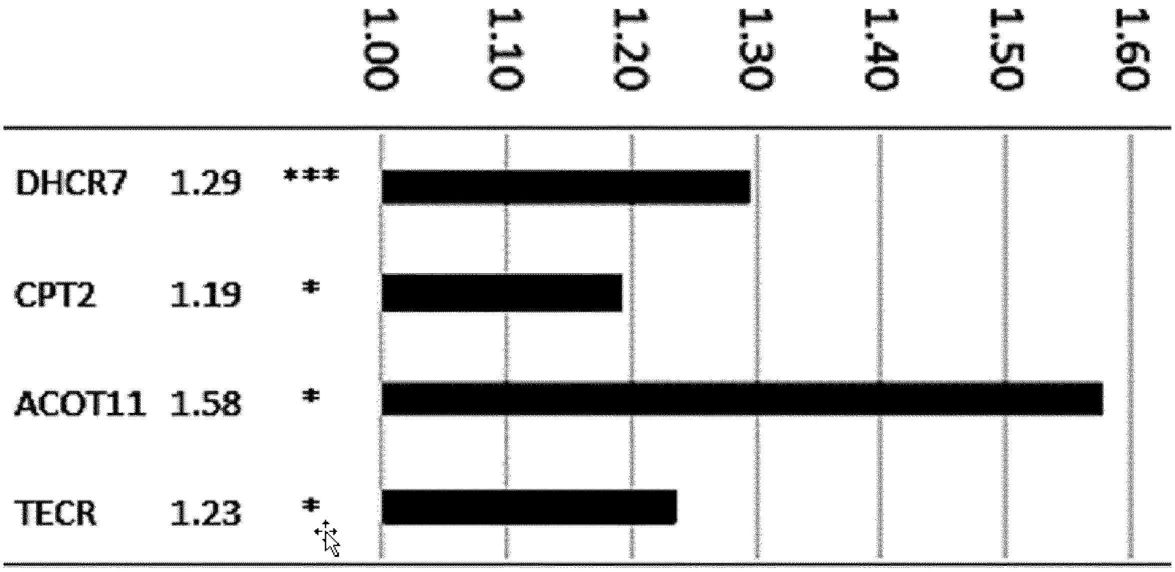

Moreover, as shown in FIG. 1B, the proteomic analysis revealed also a stimulation of cholesterol biosynthesis pathway as we found that the protein DHCR7 was upregulated. This enzyme is involved in the production of cholesterol by reduction of C7-C8 double bond of 7-dehydrocholesterol (7-DHC). The proteomic analysis showed also an upregulation of biological targets involved in fatty acids metabolism (CPT2, ACOT11 and TECR). CPT2 is involved in fatty acid beta-oxidation pathway. ACOT11 is an enzyme harboring an acyl-CoA thioesterase activity with a preference for the long chain fatty acyl-CoA thioesters hexadecanoyl-CoA/palmitoyl-CoA and tetradecanoyl-CoA/myristoyl-CoA which are the main substrates in the mitochondrial beta-oxidation pathway. TECR is an enzyme involved in both the production of very long-chain fatty acids for sphingolipid synthesis and the degradation of the sphingosine moiety in sphingolipids through the sphingosine 1-phosphate metabolic pathway. Fatty acids and sphingosine moiety are crucial for ceramides (CERs) production.

Disruption of the skin's barrier function results in a rapid and marked increase in epidermal cholesterol and fatty acids synthesis. Furthermore, inhibitors of these pathways delay the recovery of the barrier function. The increase of sphingolipids synthesis, which precedes ceramides synthesis, is more delayed than cholesterol and fatty acids, but is equally important for the restoration of skin's barrier function.

Figure 2:
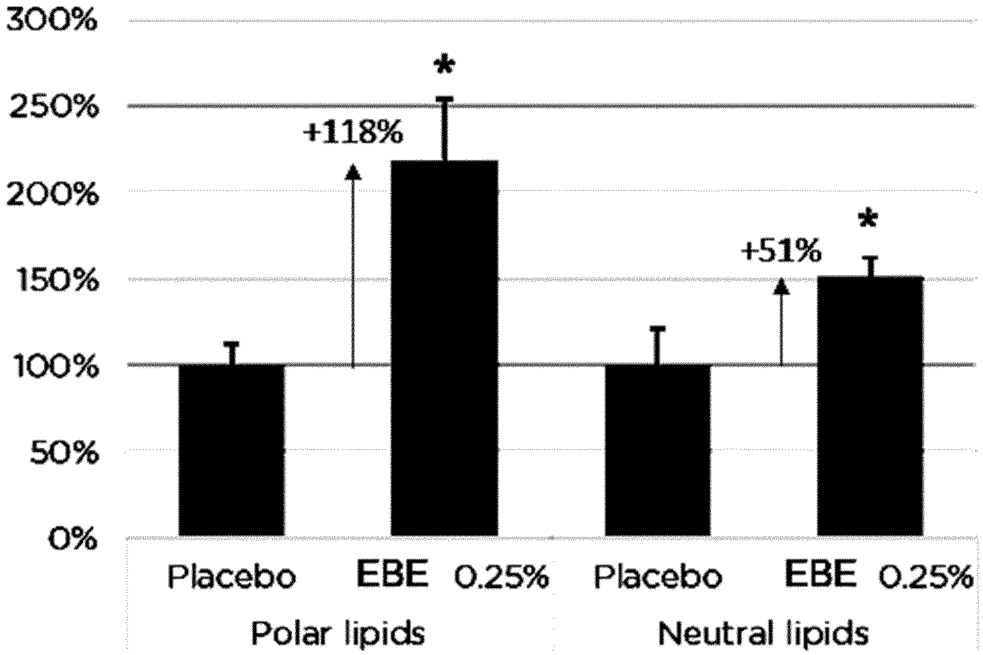
FIG. 2 shows the effect of an extract of *Bertholletia excelsa* seeds of the present invention (EBE) on a reconstructed human skin model on modulation of global lipids content.

These results provide evidence that skin lipids content, particularly cholesterol, free fatty acids and ceramides were surprisingly effectively upregulated. Consequently, the barrier function is plausibly reinforced. Indeed, the skin barrier function relies on stratum corneum lipids composition mainly dominated by these three aforementioned lipids classes.

b. EBE Stimulates Lipids Metabolism and Results in a Global Upregulation of Global Skin Lipids Content:

In order to investigate whether the global skin lipids content is effectively increased, snap frozen samples from day five timepoint were processed for lipids content visualization and quantification using known Nile Red Staining as previously described. FIG. 2 represents the modulation of global lipid content of FTS models treated with 0.25% by weight of EBE or with placebo. All measurements were performed in triplicate. Lipids content was estimated by fluorescence quantification of red fluorescence (polar lipids) and yellow-gold fluorescence (neutral lipids) with ImageJ. Statistical analysis (unpaired t-tests) were performed in comparison to the placebo, *: $p<0.05$. Nile Red is a fluorescent probe which is yellow-gold in the presence of non-polar lipids (esterified cholesterol and triglycerides) and which is red in the presence of polar lipids (phospholipids and other amphipathic lipids). Fluorescence intensity was quantified using Image J software by measuring the RawIntDen parameter in the epidermis region of interest (ROI), as shown in FIG. 2.

Results:

It was demonstrated that the upregulation of lipids metabolism highlighted in the transcriptomic and proteomic study and occurring in a variety of metabolic stages and in a variety of lipids molecules is reflected at the level of epidermis. As demonstrated, EBE upregulates both polar and non-polar lipids content of epidermis and consequently reinforces the barrier function of epidermis.

2.2. EBE Promotes a Better Skin Barrier Function Through the Promotion of the Epidermal Differentiation Process Because skin barrier function is largely insured by the stratum corneum, it is closely related to the quality of the epidermal differentiation process underwent by keratinocytes. An interesting effect is the differentiation process, the strongest is the stratum corneum and the better is the skin barrier function.

Figure 3:
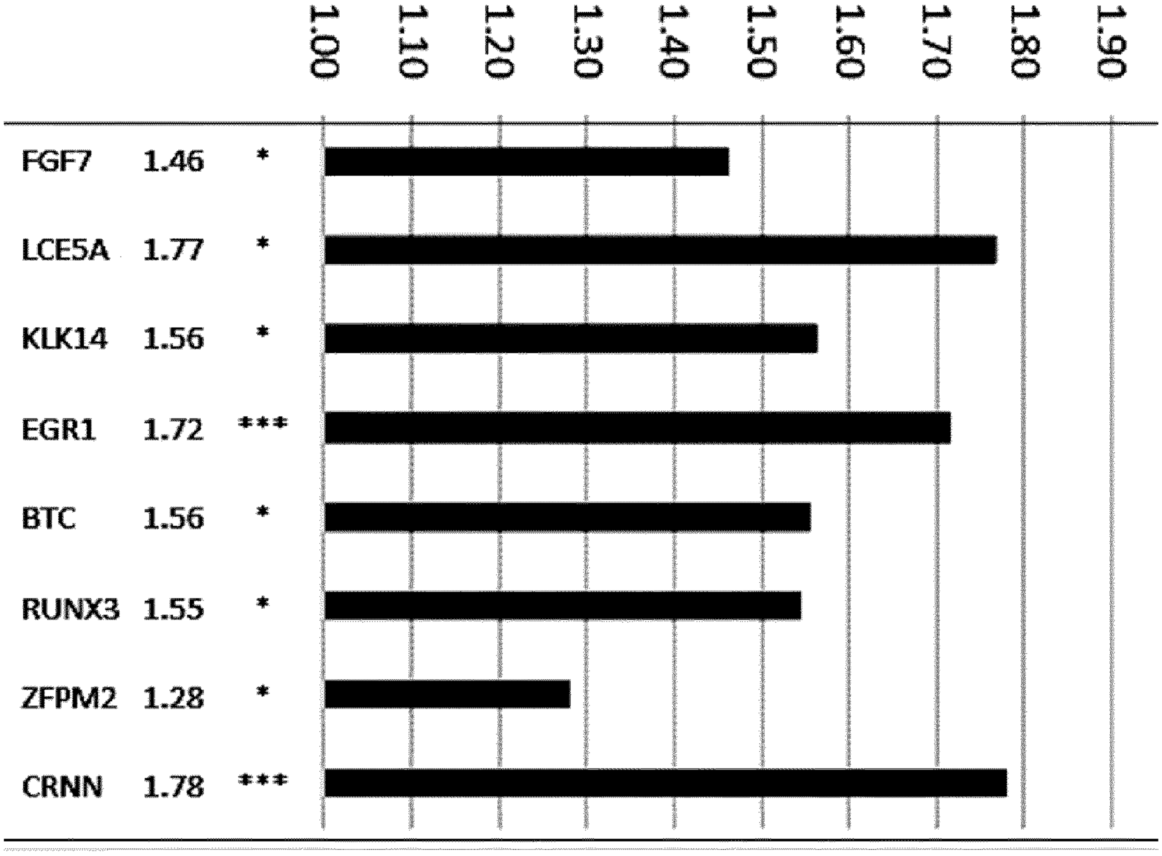
FIG. 3 shows the effect of modulation of the genes and proteins expressions involved in the epidermal differentiation process of the reconstructed human skin models treated with an extract of the present invention. The set of cellular factors comprises FGF7 (fibroblast growth factor 7), LCESA (late cornified envelope protein 5A), KLK14 (kallikrein-14), EGR1 (early growth response protein 1), BTC (probetacellulin), RUNX3 (runt-related transcription factor 3), ZFPM2 (zinc finger protein), and CRNN (cornulin).

FIG. 3 relates to the modulation of gene expression analysed by Affymetrix technology on FTS models treated with 0.25% by weight of EBE or with a placebo (Table 1). All analyses were performed in triplicate. Epidermal differentiation was highlighted by DAVID bioinformatics resources as modulated functional pathway, and the list of significantly modulated genes involved in is presented. Statistical analyses were performed in comparison to the placebo. Statistical test based on the moderated t" method implemented in the R Limma 3.26.8 package ***: $p<0.001$, *: $p<0.05$. In the same type of in vitro 3D skin model as described above, it was demonstrated that gel cream containing EBE at 0.25% by weight according to Table 1 upregulates genes involved in epidermal differentiation (FIG. 3).

Results:

It was demonstrated that by promoting the upregulation of growth factors such as FGF7, EGR1 or BTC, the extract of the present invention (EBE) promotes the renewal of epidermal cells and the promotion of their differentiation. Moreover, the upregulation of CRNN and LCESA confirm the efficiency of keratinocytes proliferation and differentiation processes. Interestingly, it was confirmed at the protein level the significant upregulation of CRNN observed at the transcription level.

2.3. EBE Reinforces Skin Barrier Function by Regulating Keratinocytes Cohesion, and Cytoskeleton As the viable epidermis plays also a crucial role in the skin barrier function, it was studied the effect of EBE on this level. Indeed, the viable epidermis exerts the skin barrier function thanks to the cell-cell cohesion, and the cell cytoskeleton, which is a real scaffold for the cell. Moreover, three cytoskeleton structural components the microtubules, actin microfilaments, and intermediate filaments are directly linked to cell junctions, showing their peculiar interest for skin barrier function.

Figure 4:
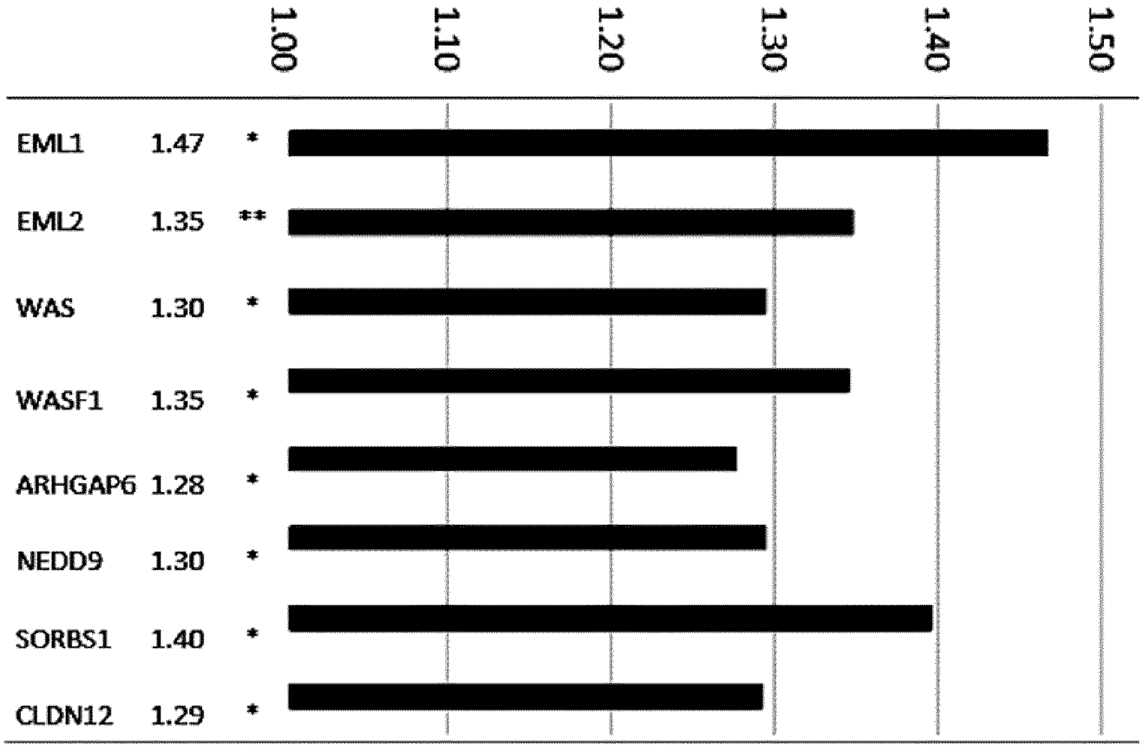
FIG. 4 demonstrates the modulation of the genes and proteins expressions involved in regulation of keratinocytes cohesion and cytoskeleton of the reconstructed human skin models treated with an extract of the present invention. The set of cellular factors comprises EML1 (echinoderm microtubule-associated protein-line 1), EML2 (echinoderm microtubule-associated protein-line 2), WAS (Wiskott-Aldrich syndrome protein), WASF2 (Wiskott-Aldrich syndrome protein family member 1), ARHGAP6 (Rho GTPase-activating protein 6), NEDD9 (enhancer of filmentation 1), SERBS1 (sorbin and SH3 domain-containing protein 1), and CLDN12 (claudin 12).

FIG. 4 relates to the modulation of gene expression analysed by Affymetrix technology on FTS models treated with 0.25% by weight of EBE or by a placebo (table 1). All analyses were performed in triplicate. Cell junctions and cytoskeleton were highlighted by DAVID bioinformatics resources as modulated functional pathways, and the list of significantly modulated genes involved in is presented. Statistical analyses were performed in comparison to the placebo. Statistical test based on the moderated t" method implemented in the R Limma 3.26.8 package. **: $p<0.01$, *: $p<0.05$.

Figure 5:
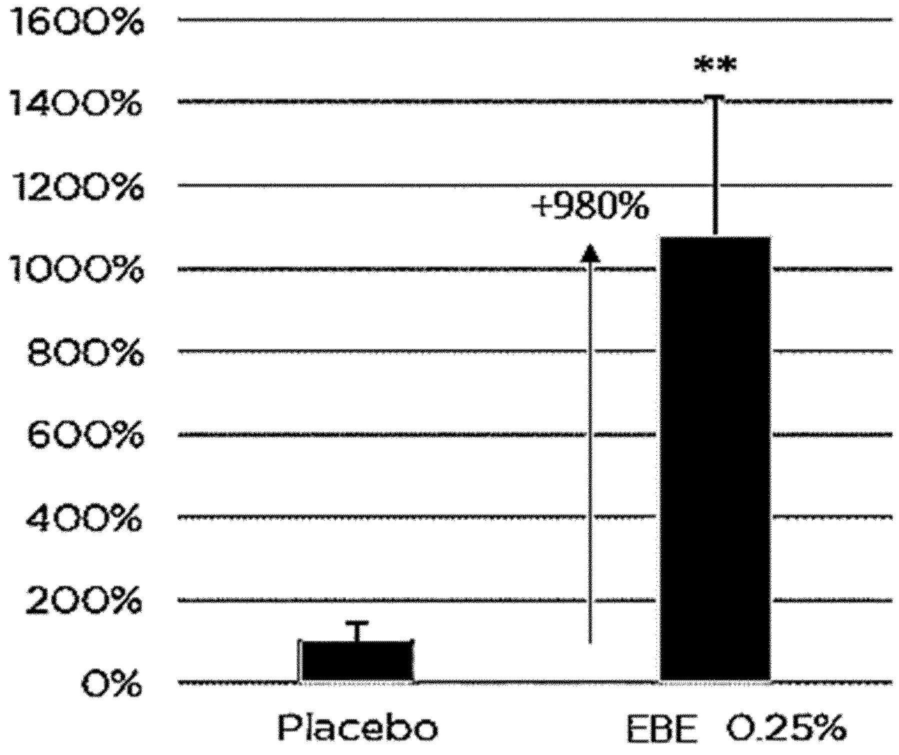
FIG. 5 shows the modulation of the keratin 10 (K10) protein expression in the reconstructed human skin models treated with an extract of the present invention.

FIG. 5 relates to the modulation of keratin 10 (K10) expression analysed by immunofluorescence on FTS models treated with 0.25% by weight of EBE or by a placebo (Table 1). All measurements were performed in triplicate. K10 expression was estimated by fluorescence quantification with ImageJ. Statistical analysis (Mann-Whitney) was done in comparison to the placebo (**: $p<0.01$).

Results:

Interestingly, it was surprisingly found that the EBE upregulates the transcriptional expression of tight junction's components (such as SORBS 1, and NEDD9) (FIG. 4). SORBS1 is the gene coding for Ponsin protein, which is crucial in the cell adhesion process, due to its interaction with numerous proteins located in tight junctions' structures. These tight junction components may all have a role in cytoskeleton organization. For example, it is known that Ponsin mediates the organization of actin cytoskeleton and NEDD9 is involved in the assembly of actin fibers. It was demonstrated that EBE upregulates also the expression of Claudin-12. The family of claudins proteins are the main constituents of tight junctions and interact also with the cytoskeleton. Moreover, EBE upregulates also the expression of EML1 and EML2, two members of EMLs family. The EMLs are a conserved family of microtubule-associated proteins (MAPs) involved in microtubule binding, assembly and regulation. While, it is known that EML1 modulates the assembly and organization of the microtubule cytoskeleton, EML2 binds microtubules and promotes microtubules dynamics to allow the evolution of the cytoskeleton. It was observed also a significant modulation of mRNA transcripts of WAS and WASF1 by EBE. It is known that these two transcripts belong to the WASP family proteins, required for normal cytoskeletal function. WAS and WASF1 (are implicated in actin polymerization and thus formation of actin filaments. In parallel, EBE stimulates also a Rho GTPase-activating protein the ARHGAP6, which is known to be a very important in cytoskeletal organization. Interestingly, this Rho GTPase-activating protein ARHGAP6 is a cytoskeletal protein that promotes actin remodelling.

Finally, it was demonstrated that EBE upregulates the translation of K10, a cytoskeleton crucial protein in epidermis differentiation process (FIG. 5). Keratins belong to intermediate filaments, a cytoskeleton component. It is agreed that keratins confer mechanical resilience on epidermis, forming intracellular filament meshworks linked into desmosome cell junction. K10 is one of the most keratin found in intermediate filaments of differentiated keratinocytes in the stratum spinosum and stratum granulosum. It was demonstrated that lacking K10 exhibits larger-than-normal suprabasal keratinocytes and defective flattening. Defects in K10 are known to contribute to barrier defect proving, consequently, the importance of K10 in cytoskeleton, cell junction and the resulting barrier functionality.

2.4. EBE Regulates the Inflammatory Pathways in the Skin

Figure 6:
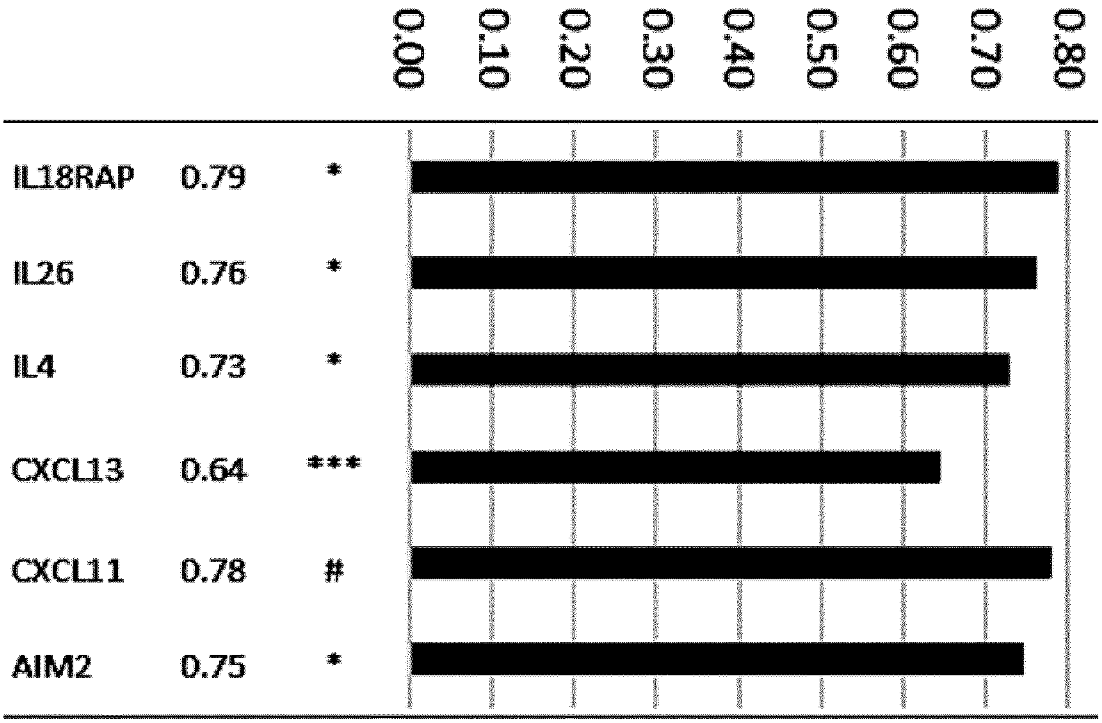
FIG. 6 shows the modulation of the genes expressions involved in the regulation of the inflammatory pathways of the reconstructed human skin models treated with an extract of the present invention. The set of cellular factors comprises IL18RAP (interleukin 18 receptor accessor protein), IL26 (interleukin 26), IL4 (interleukin 4), CXCL13 (C-X-C motif chemokine ligand 13), CXCL11 (C-X-C motif chemokine ligand 11), and AIM2 (absent in melanoma 2).

In order to investigate whether EBE is enabling to alleviate skin inflammation, which is part of a skin disorder, it was performed the same studies by using the transcriptomic method, the same material (reconstituted skin) in the same conditions as set forth in paragraph 2.3 above. FIG. 6 relates to the modulation of the genes expressions related to inflammatory pathways analysed by Affymetrix technology on FTS models treated with 0.25% by weight of EBE or by placebo (Table 1). All analyses were performed in triplicate. The list of the significantly modulated genes involved in inflammation is presented. Statistical analyses were performed in comparison to the placebo. Statistical test based on the moderated t" method implemented in the R Limma 3.26.8 package **: $p<0.01$, *: $p<0.05$.

Results:

It was surprisingly found that EBE down regulates the mRNA expression of several biological markers involved in inflammasome activation (AIM-2) and IL-18 dependent signaling, such as IL18RAP, IL-26, IL-4 and CXCL13, but also in JAK/STAT signaling pathway where the CXCL11 chemokine is stimulated (C-X-C motif chemokine ligand 11), two signaling pathways upregulated in dermatological diseases such as psoriasis, atopic dermatitis presenting a well-described defect in barrier function. Additionally, it was also demonstrated a down regulation of granulocyte-macrophage colony-stimulating factor 1 expression in the proteomic analysis.

3. Cosmetic Formulation Example

A gel cream comprising an extract of the at least partly deoiled press residue of *Bertholletia excelsa*, according to the Table 1, suitable for a topical application is prepared according to a conventional method.

4. In Vivo Study

The following study aims to demonstrate the ability of extract of *Bertholletia excelsa* seeds of the present invention (EBE) to restore the skin barrier function.

4.1 EBE Promotes the Skin Barrier Recovery

The stimulatory effect of EBE on barrier recovery was assessed by the mean of in vivo study on 15 healthy women aged from 29 to 65 years old, with a mean age of 44±11. In order to generate a skin barrier default, tape stripping was realized on the forearm as many as necessary to reach a TransEpidermal Water Loss (TEWL) value of 20, with a limit of 20 strips. This skin barrier disruption was done in three areas. Mean value of TEWL before tape stripping was 9.88±2.64. One of the areas received an application of EBE formulated at 1%, another area received the placebo as described in the Table 2 below, and a third area was non-treated. TEWL measurements were performed on the three areas, three hours after to evaluate the skin barrier recovery.

As used herein, TEWL is the amount of water that passively evaporates from inside the skin to outside due to water gradient differences on both side of the skin barrier. TEWL was the parameter used to evaluate skin barrier recovery. An integer barrier is able to retain water whereas a disrupted barrier is responsible for a higher water loss.

TEWL measurements were performed using a Tewameter TM300™ (Courage & Khazaka electronics) which measured the water evaporated from skin in $g/cm^2$. Twenty consecutive values were measured, the mean value was calculated.

TABLE 2

Gel cream containing EBE at 1% by weight, and placebo

| Composition of gel cream in (% weight) | Placebo | EBE at 1% by weight |
|---|---|---|
| Water | 96.00 | 95.00 |
| Ammonium Acryloyldimethyltaurate/VP Crosspolymer | 0.80 | 0.80 |
| Dicaprylyl Ether | 1.00 | 1.00 |
| Aqueous buffer of Citric Acid and Sodium Citrate | 1.00 | 1.00 |
| Glycerin, Water, EBE | 0.00 | 1.00 |
| Phenoxyethanol and Methylparaben and Ethylparaben | 1.10 | 1.10 |
| Fragrance | 0.10 | 0.10 |

The skin barrier is able to recover naturally in three hours as skin has an intrinsic repair metabolism to protect the body.

Figure 7:
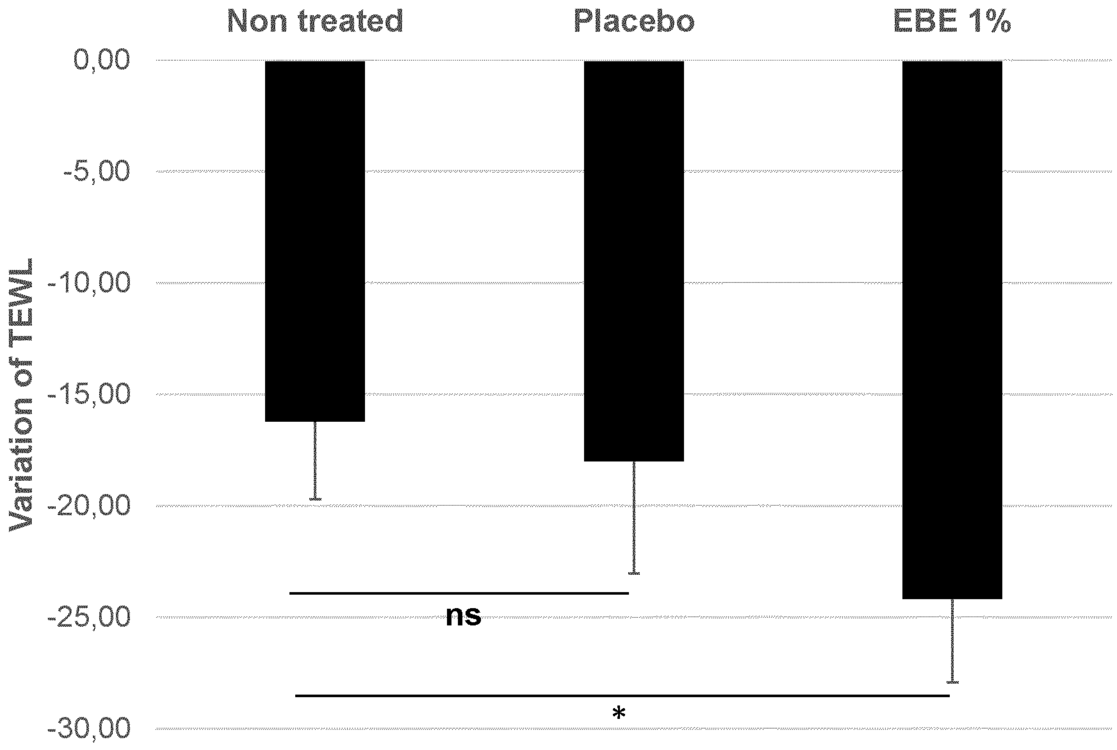
FIG. 7 relates to the barrier recovery of forearm's skin of volunteers disrupted with tape stripping to reach a TransEpidermal Water Loss (TEWL) value of at least and then treated with placebo formulation or a formulation containing an extract of *Bertholletia excelsa* seeds of the present invention (EBE).

FIG. 7 shows that the skin barrier recovery of the area treated with placebo was essentially not different from the non-treated one, showing that the empty formulation has no effect on skin barrier recovery. As a consequence, it was surprisingly found that EBE promotes the recovery of the skin barrier function as TEWL value is significantly lowest than the one obtained without any formula in 3 hours after disruption. This result confirms that EBE is able to improve the skin barrier function by promoting a better recovery.

The invention claimed is:

1. An extract of *Bertholletia excelsa* seeds obtainable from extracting an at least partly deoiled press residue of *Bertholletia excelsa* seeds having an oil content lower than the oil content in *Bertholletia excelsa* seeds before pressing with a hydroalcoholic solvent,
   wherein the extract comprises at least 1.5% by weight, referred to the total weight of the dry content of the extract, of one or more polyphenols, wherein the residual oil content is more than 15% and less than 50% by weight to the oil content referred to the *Bertholletia excelsa* seeds before pressing
   wherein the hydroalcoholic solvent contains between 50 and 82% (v/v) alcohol, and
   wherein the solids content in the extract represents at least 0.1% by weight, referred to the total weight of the extract.

2. The extract of claim 1, wherein the at least partly deoiled press residue is obtained from pressed fresh *Bertholletia excelsa* seeds.

3. The extract of claim 1, wherein the hydroalcoholic solvent is selected from mixtures of ethanol, glycerol, or propane diol with water or an aqueous buffer.

4. The extract of claim 1, wherein the hydroalcoholic solvent is a mixture of ethanol and water, or a mixture of ethanol and an aqueous buffer.

5. The extract of claim 1 wherein the at least partly deoiled press residue comprises a residual oil content more than 15 to 45% by weight, referred to the *Bertholletia excelsa* seeds before pressing.

6. A method for preparing an extract of *Bertholletia excelsa* seeds of claim 1 comprising the following successive steps:
   (i) providing an at least partly deoiled press residue of *Bertholletia excelsa* seeds, comprising a residual oil content more than 15% and less than 50% by weight referred to the *Bertholletia excelsa* seeds before pressing, wherein the at least partly deoiled press residue is optionally dried;
   (ii) contacting the deoiled press residue with a hydroalcoholic solvent, wherein the hydroalcoholic solvent contains between 50 and 82% (v/v) alcohol;
   (iii) enabling homogenization of the deoiled press residue within the hydroalcoholic solvent for 30 minutes to 2 hours, at 15 to 30° C.;
   (iv) separating the extract from the solid residuals of step (iii), by means of filtration or centrifugation; and
   (v) concentrating the extract by removing the at least one solvent or parts thereof.

7. A cosmetic or pharmaceutical composition comprising:
   (A) the extract of *Bertholletia excelsa* seeds of claim 1 as an active ingredient; and
   (B) at least one further cosmetically and/or pharmaceutically acceptable ingredient other than the extract of *Bertholletia excelsa* seeds,
   wherein the composition is a composition for topical use selected from the group consisting of a solution, a suspension, an emulsion, a cream, a paste, a gel, a lotion, a powder, a soap, a surfactant-containing water, an oil, a shampooing, and a spray, or wherein the composition is a nutraceutical composition which is administered orally.

8. The cosmetic or pharmaceutic composition of claim 7, wherein the composition comprises 0.0001 to 20% by weight, referred to the total weight of the composition, of the extract of *Bertholletia excelsa* seeds.

9. A method for reinforcing, for preserving, and/or for restoring the skin barrier function, for improving the skin hydration, for preventing and/or mitigating skin aging, and/or for alleviating and/or for preventing skin disorders or damages, comprising administering a therapeutically effective amount of the extract of *Bertholletia excelsa* seeds of claim 1, to a patient in need thereof.

10. The extract of claim 1, wherein the extract comprises at least 3% by weight, referred to the total weight of the dry content of the extract, of one or more polyphenols.

11. The extract of claim 10, wherein the solids content in the extract represents at least at least 1.5% by weight, referred to the total weight of the extract.

12. The extract of claim 11, wherein the at least partly deoiled press residue comprises a residual oil content more than 20 to 35% by weight, referred to the *Bertholletia excelsa* seeds before pressing.

* * * * *